US006382209B1

(12) United States Patent
Toye

(10) Patent No.: US 6,382,209 B1
(45) Date of Patent: May 7, 2002

(54) APPARATUS AND METHOD ENABLING LOCATION OF TRACHEA BREATHING TUBE IN BODY VISCUS

(76) Inventor: Frederic J Toye, 1809 Termino Ave., Apt. 5201, Long Beach, CA (US) 90815

( * ) Notice: Subject to any disclaimer, the term of this patent is extended or adjusted under 35 U.S.C. 154(b) by 0 days.

(21) Appl. No.: 09/418,105

(22) Filed: Oct. 14, 1999

(51) Int. Cl.⁷ .............................................. A61M 16/00
(52) U.S. Cl. ........................... 128/207.14; 428/207.29; 428/200.26
(58) Field of Search ..................... 128/207.14, 207.29, 128/200.26; 604/96.01, 160, 161, 187, 264, 272; 606/191, 192, 196, 167, 108

(56) References Cited

U.S. PATENT DOCUMENTS

| | | | | |
|---|---|---|---|---|
| 2,865,374 A | * | 12/1958 | Brown et al. | 128/305 |
| 2,991,787 A | * | 7/1961 | Shelden et al. | 128/351 |
| 3,384,087 A | | 5/1968 | Brummelkamp | |
| 3,511,243 A | | 5/1970 | Toy | |
| 3,677,243 A | * | 7/1972 | Nerz | 128/214.4 |
| 3,817,250 A | * | 6/1974 | Weiss et al. | 128/305 |
| 4,147,165 A | * | 4/1979 | Tauschinski | 128/214.4 |
| 4,246,897 A | * | 1/1981 | Muto | 128/207.15 |
| 4,364,391 A | | 12/1982 | Toye | |
| 4,411,654 A | * | 10/1983 | Boarini et al. | 604/165 |
| 4,412,832 A | * | 11/1983 | Kling et al. | 604/164 |
| 4,471,778 A | | 9/1984 | Toye | |
| 4,498,473 A | * | 2/1985 | Gereg | 128/207.15 |
| 4,520,810 A | * | 6/1985 | Weiss | 128/200.26 |
| 4,581,025 A | * | 4/1986 | Timmermans | 604/264 |
| 4,596,559 A | * | 6/1986 | Fleischhacker | 604/170 |
| 4,677,978 A | * | 7/1987 | Melker | 128/207.14 |
| 4,869,718 A | * | 9/1989 | Brader | 604/164 |
| 4,913,704 A | * | 4/1990 | Kurimoto | 604/171 |
| 4,978,334 A | | 12/1990 | Toye et al. | |
| 5,098,392 A | * | 3/1992 | Fleischhacker et al. | 604/165 |
| 5,167,634 A | * | 12/1992 | Corrigan, Jr. et al. | 604/160 |
| 5,171,222 A | * | 12/1992 | Euteneuer et al. | 604/102 |
| 5,217,005 A | * | 6/1993 | Weinstein | 128/200.26 |
| 5,221,263 A | * | 6/1993 | Sinko et al. | 604/161 |
| 5,250,033 A | * | 10/1993 | Evans et al. | 604/160 |
| 5,279,285 A | * | 1/1994 | Griggs | 128/200.26 |
| 5,653,230 A | * | 8/1997 | Ciaglia et al. | 128/207.15 |
| 5,996,582 A | * | 12/1999 | Turnbull | 128/207.29 |
| 6,077,248 A | * | 6/2000 | Zumschlinge | 604/169 |
| 6,148,818 A | * | 11/2000 | Pagan | 128/207.15 |

OTHER PUBLICATIONS

T. Kolobow et al "New Ultrathin—Walled Endotracheal Tube with a Laryngeal Seal Design" *Anesthesiology* vol. 84 No. 1, Jan. 4, 1996.

* cited by examiner

*Primary Examiner*—John G. Weiss
*Assistant Examiner*—Mital Patel
(74) *Attorney, Agent, or Firm*—Joseph F. McLellan

(57) ABSTRACT

An apparatus and method employing a syringe mounted splittable needle insertable through body tissue to provide a percutaneous passage through the body tissue and into a cavity such as a trachea. After insertion of the needle, the syringe is separated from the needle and a dilator is fitted in its place. The distal extremity of the dilator includes a leader which extends through the needle and into the trachea. The midportion of the dilator supports the distal extremity of a flexible, ultra thin trachea tube. The tube is large enough in diameter that it can be fitted over the distal end of the dilator and moved in a proximal direction toward the dilator midportion. Further movement onto the dilator is prevented by engagement of a smaller diameter distal extremity of the tube with a larger diameter stop section located on the dilator midportion adjacent its distal extremity. The needle is split to allow separation of the needle from the dilator and tube, followed by thrusting of the dilator and tube farther into the trachea. The dilator is then withdrawn to leave the tube in position within the trachea for ventilation of the trachea upper airway. An annular inflatable cuff is affixed to the trachea tube for occluding the space between the trachea tube and the inner tracheal wall, and for providing additional stiffness at the distal end of the trachea tube.

2 Claims, 4 Drawing Sheets

APPARATUS AND METHOD ENABLING LOCATION OF TRACHEA BREATHING TUBE IN BODY VISCUS

BACKGROUND OF THE INVENTION

1. Field of the Invention

The present invention relates to an apparatus and method for performing a percutaneous or non-dissection procedure enabling passage or entry of a trachea breathing tube into a body cavity or viscus.

2. Description of the Prior Art

A number of devices have been advanced for non-dissection establishment of passages into a body cavity or hollow viscus, particularly for tracheostomies. Such devices are normally preferable to dissection procedures, which require considerable surgical skill to prevent profuse bleeding of the involved blood vessels during a the procedure.

U.S. Pat. No. 3,511,243 (Toye) discloses a method and apparatus using a dilator to which a flexible leader is separably attached. A hollow needle is first inserted into the trachea. The distal extremity of the leader is passed through the needle into the trachea and the needle is discarded. An inner guide is telescoped into a relatively inflexible, outer guide or breathing tube which forms a smooth continuation of the outer guide. The guides are forced through body tissue and into the trachea along the path defined by the leader. The inner guide is then withdrawn, removing the leader with it. However, this does not result in withdrawal of the breathing tube because the inflexibility of the plastic material of the breathing tube enables its easy separation from the inner guide. The outer guide or breathing tube is now located in the trachea whereby the patient can breath air through the breathing tube. The method is somewhat complex because it involves a precise sequence of steps which require training to perform properly.

U.S. Pat. No. 4,364,391 (Toye) discloses a related but somewhat less involved procedure. An inner needle is telescoped within a slotted outer needle and the two needles are inserted into the trachea using a syringe attached to the inner needle. The syringe and attached inner needle are withdrawn, leaving the slotted outer needle in place. A leader attached to a dilator is fed through the outer needle and into the trachea. The dilator is telescoped within a trachea breathing tube. The outer needle is next withdrawn from the trachea, and the leader is simultaneously laterally stripped from the outer needle through the outer needle slot. The dilator and breathing tube are then forced into the trachea, using the leader as a guide. Finally, the dilator and its attached leader are withdrawn. The breathing tube is relatively inflexible so that it separates easily from the dilator and is left in position within the trachea. Use of the slotted outer needle enables more simplified prior attachment of the leader to the dilator, compared to the procedure of U.S. Pat. No. 3,511,243, but the procedure of U.S. Pat. No. 4,364,391 nevertheless requires significant training to perform properly.

An outgrowth of the foregoing procedures is the method and apparatus of U.S. Pat. No. 4,471,778 (Toye). Rather than using two needles, a single splittable needle receives the dilator leader. More particularly, the single needle is inserted through the body tissue with a syringe, and the dilator leader is inserted through the splittable needle into the trachea. The dilator is laterally disposed through an opening made in the side of a breathing tube, and extends out the end of the breathing tube. After insertion of the leader, the needle is split and removed. The dilator is thrust into the trachea, carrying the breathing tube with it. Finally the dilator and attached leader are separated from the breathing tube. The breathing tube is made of relatively inflexible material and is easily movable independently of the dilator so that the tube is left in position within the trachea.

Although the use of a splittable needle and lateral entry dilator is a procedure simpler than the procedures of the previously mentioned patents, certain complexities still remained.

U.S. Pat. No. 4,978,334 (Toye et al) is yet another improvement involving a needle mounted to a syringe that is telescoped within the central bore of a dilator. The dilator in turn is telescoped within a trachea tube.

After the needle and dilator tip are inserted into the trachea, the needle is removed from the dilator, leaving the dilator and surrounding trachea tube partially extending into the trachea. The dilator and trachea tube are then thrust farther into the trachea, and the dilator removed through the open proximal end of the trachea tube. Removal of the dilator does not result in removal of the tube because the material of the tube is relatively stiff and easily separable from the dilator so that the tube can be left in position within the trachea.

The present invention is a further improvement upon the foregoing procedures. It utilizes a very flexible thin wall wire reinforced trachea tube in combination with a splittable syringe needle. The thin wall provides an enlarged passage in the breathing tube, which dramatically increases the capacity of the tube to carry air and thereby better meet the breathing needs of a patient.

SUMMARY OF THE INVENTION

In accordance with the present invention, the apparatus and method employ a single syringe mounted splittable needle. The needle provides a percutaneous passage through body tissue and into a body cavity such as a trachea. In this procedure the syringe and needle are inserted into the trachea. The syringe is then removed once aspiration confirms proper location of the needle within the trachea. A special dilator is attached to the needle in place of the syringe. The dilator includes a small diameter leader at its distal extremity which is adapted to be inserted into the trachea through the needle. The opposite or proximal extremity of the dilator includes a handle or knob for pulling the dilator out of the trachea.

The smaller diameter distal extremity of the dilator smoothly increases in diameter to join the dilator midportion. The result is a tapered transition zone or retention seat which defines a stop section or constraining means. Beyond this constraining means the midportion is of generally constant diameter up to the proximal extremity of the dilator.

A flexible, generally cylindrical, ultra thin walled, wire reinforced trachea tube is mounted to the dilator for insertion into the trachea along with the dilator. The major portion of this tube is larger in diameter than the diameter of the dilator. Consequently, the tube can be pushed in a proximal direction over the smaller diameter dilator. However, the distal extremity of the tube is of reduced diameter compared to the dilator at the constraining means. Therefore, the distal extremity of the tube cannot move in a proximal direction beyond the constraining means.

The dilator leader is passed through the needle and into the trachea. The needle is then split apart so that it can be separated from the dilator and removed. The dilator and the tube which is mounted to the dilator are next thrust farther into the trachea. During this step the larger diameter of the dilator constrains the smaller diameter distal end of the very flexible tube from sliding up on the dilator in accordion fashion when the dilator is forced through body tissue into the tracheal area.

The dilator is pulled out of the tube and trachea by means of a dilator handle. During dilator removal the pressure of surrounding body tissue on the tube is sufficient to constrain the tube against proximal movement with the dilator, so that the dilator can be separated from the tube and removed.

The ultra thin walled breathing tube and certain of its advantages are discussed in U.S. Pat. No. 5,537,729, but insofar as applicant is aware there is no teaching or suggestion in the patent or in the art respecting how such a very flexible, longitudinally collapsible tube can be combined with a dilator and needle in a manner enabling rapid placement of the tube within the trachea.

Other objects and features of the invention will become apparent from consideration of the following description taken in connection with the accompanying drawings.

DESCRIPTION OF THE PREFERRED EMBODIMENTS

As will be seen from the description which follows, the present apparatus and method are employed to perform a percutaneous tracheostomy.

The method utilizes a single #14 splittable needle 10 which is mounted to a syringe 20. The plunger 23 of the syringe is withdrawn to evacuate air, thereby verifying proper location of the needle in the tracheal lumen.

The method utilizes a single #14 splittable needle 10 which is mounted to a syringe. The plunger of the syringe is withdrawn to evacuate air, thereby verifying proper location of the needle in the tracheal lumen.

Figure 1:
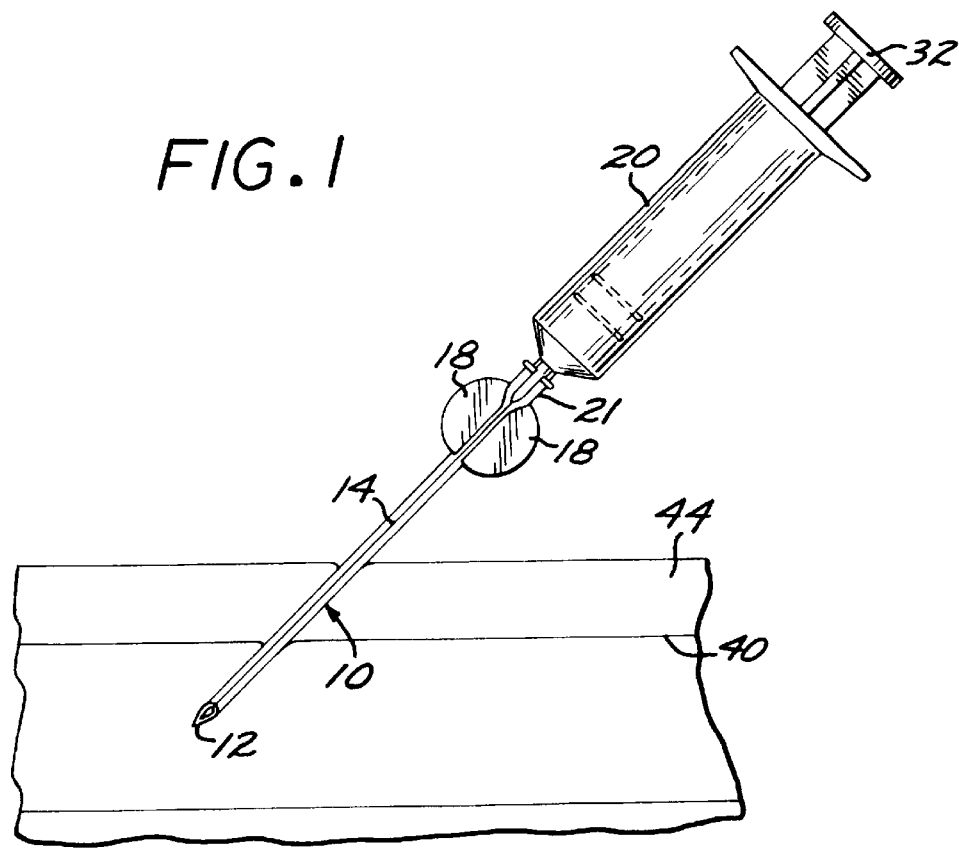
FIG. 1 is an elevational view of a syringe and splittable needle inserted into a tracheal lumen in a tracheostomy or similar procedure.
Figure 2:
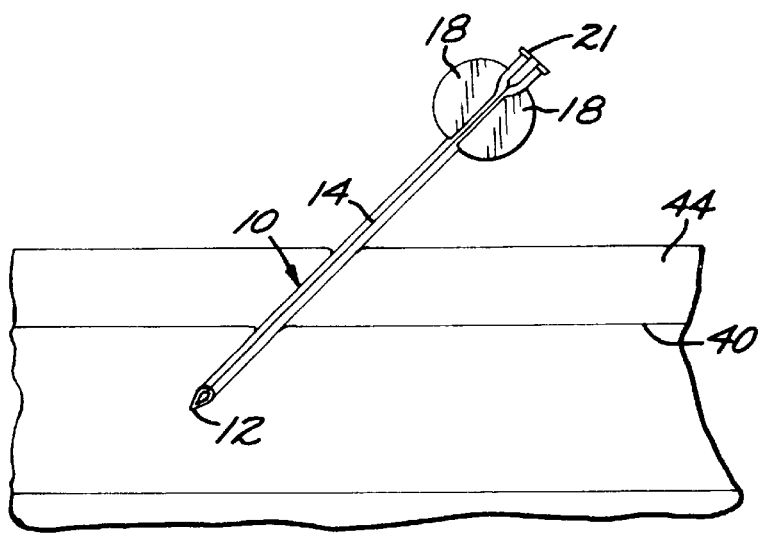
FIG. 2 is a view similar to FIG. 1, but showing the needle in the trachea after the syringe is removed.
Figure 6:
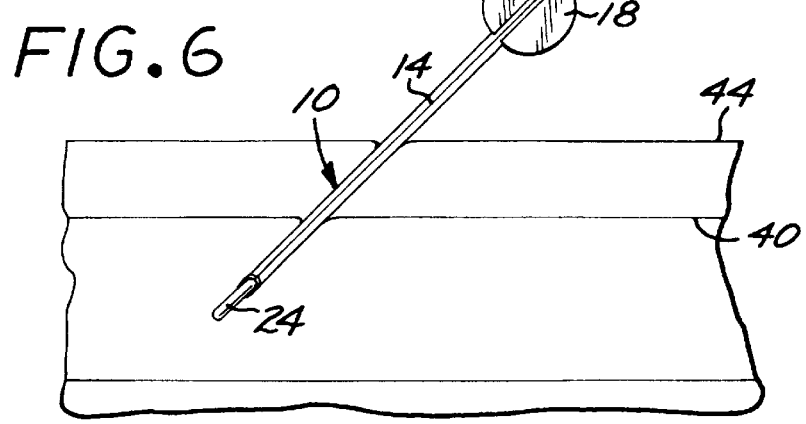
FIG. 6 is a view similar to FIG. 9, but illustrating the dilator mounted to the splittable needle.

As seen in FIGS. 1, 2 and 6, the needle 10 has a sharp distal end which is cut on the bias to facilitate its penetration of the trachea and associated tissue and cartilage. The needle includes a central bore 12 for the dilator leader, as will be seen, and the needle is structurally weakened longitudinally by providing a very narrow width groove or scoring at 14, as seen in FIG. 1. The particular means for structurally weakening the needle may vary according to the particular needle design, and the present invention therefore should not be construed as limited to the needle weakening method shown or the needle size mentioned.

Figure 8:
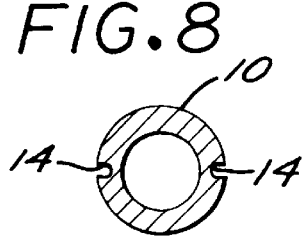
FIG. 8 is an enlarged view of the needle prior to splitting it open.
Figure 9:
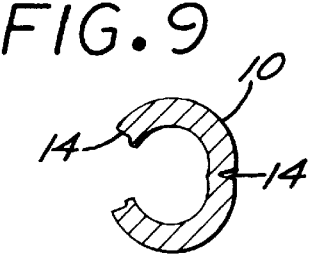
FIG. 9 is a view similar to FIG. 8, illustrating the split open needle.
Figure 10:
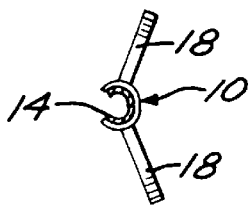
FIG. 10 is a view similar to FIG. 7, illustrating the orientation of the needle structure after splitting.
Figure 11:
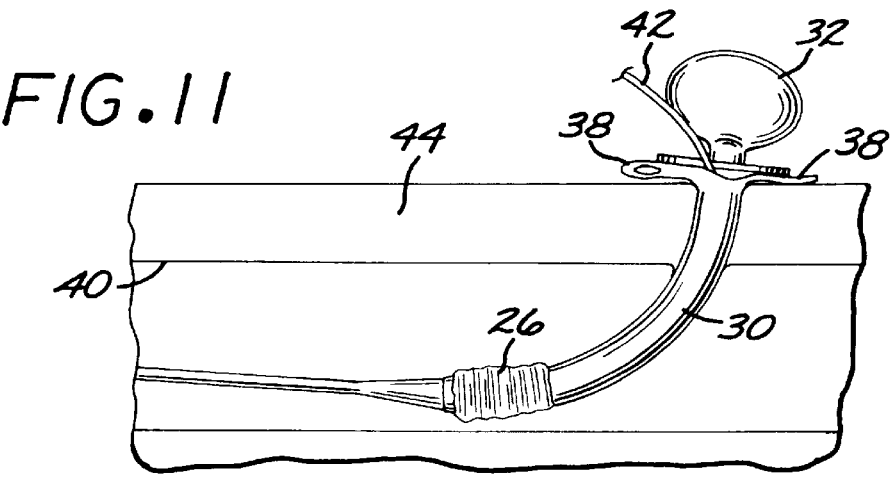
FIG. 11 is a view illustrating the dilator and trachea breathing tube after placement of the dilator and breathing tube in the trachea.

A pair of metal spreader tabs 18 are spot welded or otherwise rigidly affixed at their ends to the needle 10 on opposite sides of the score line 14, as best seen in FIGS. 1, 2, 7 and 10. If desired, the tabs 18 could be a single length of metal extending around the needle 10. The needle is split by pushing or snapping together the tabs 18 and then drawing them apart. This alters the original configuration shown in FIG. 8 to that of FIG. 9.

The proximal end of a usual and conventional syringe 20 (30 cc being a suitable size), is fitted within a syringe socket or receiver 21 on the distal end of the needle 10. The syringe 20 is manipulated to insert the attached needle through the tracheal wall 40 and into the tracheal lumen, the proper location being signaled, as previously indicated, when the care giver is able to aspirate air through the needle.

Figure 7:
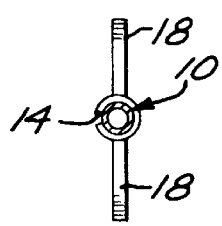
FIG. 7 is an enlarged cross section view of the needle, showing the spreader tabs.

Once it has been determined that the needle 10 is in proper position, the syringe 20 is removed and a special elongated dilator 22 is mounted in its place within the needle receiver socket 21, as seen in FIG. 7.

Figure 3:
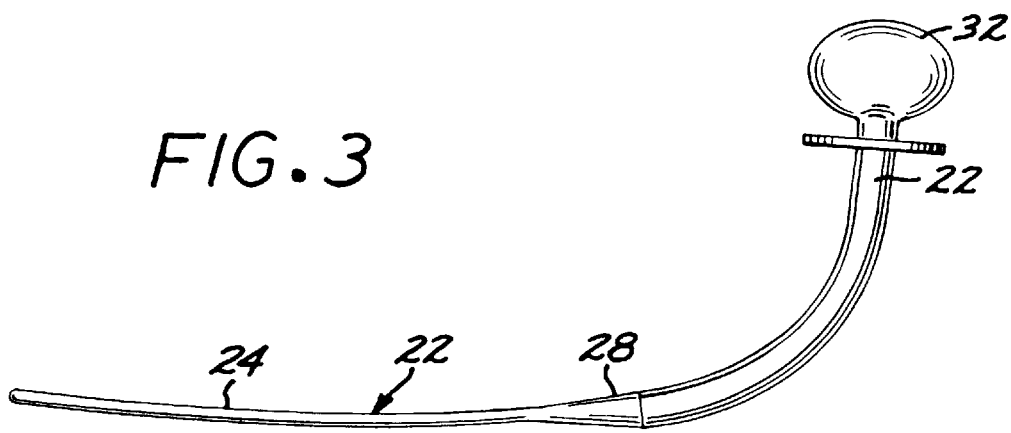
FIG. 3 is an enlarged view of a special dilator whose distal extremity includes a leader for passage through the needle and into the trachea.
Figure 4:
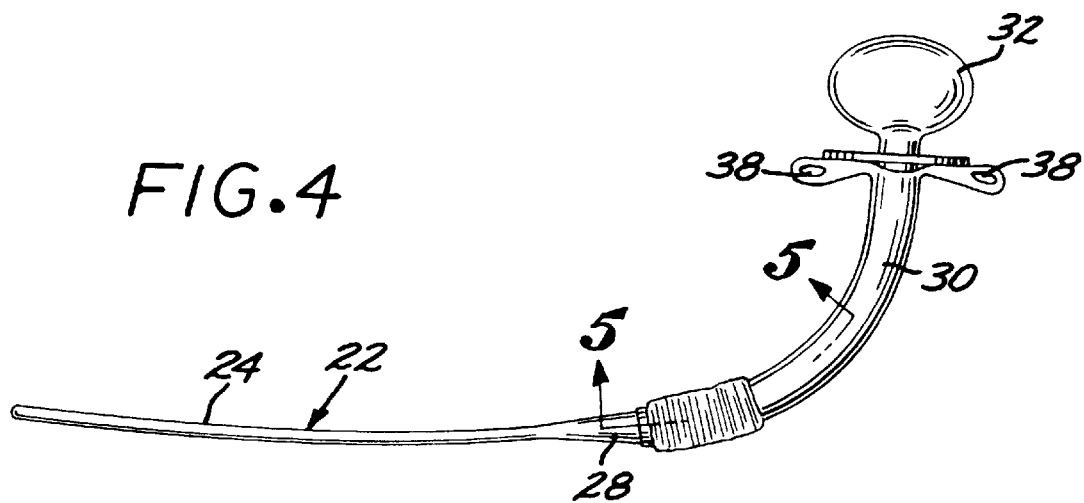
FIG. 4 is a view similar to FIG. 3, but illustrating a trachea tube pulled distally over the dilator leader and onto the dilator midportion, the tube being constrained against further movement by engagement between the smaller distal extremity of the tube and a larger dilator stop action.

As seen in FIGS. 3 and 4, the proximal end of the dilator 22 includes a knob or handle 32, and the distal end of the dilator 22 includes an integral leader 24 which is projected through the needle and into the trachea. The leader is of substantially constant cross section, but gradually increases in diameter in the direction of the distal extremity of the dilator midportion.

The dilator leader is made of plastic material flexible enough to be easily threaded into the open upper end of the needle bore and projected into the tracheal lumen. The flexibility of the leader 24 enables it to align itself with the trachea.

The constant diameter portion of the leader 24 constitutes approximately one third of the length of the dilator 22. In a proximal direction, as indicated above, the cross sectional diameter of the dilator gradually increases to form a tapered, conical surface which together with a reduced diameter portion of a trachea tube 30, constitutes a constraining means, as will be seen.

Before the dilator 22 is mounted to the needle 10, as shown in FIG. 7, a wire reinforced, extremely flexible, ultra thin, generally cylindrical and hollow breathing or trachea tube 30 is fitted over the distal extremity of the dilator 22. The distal extremity of the tube 30 is pulled onto the dilator 22 by means of a pair of tabs or handle means 38. The handle means 38 may be formed by splitting both sides of the end of the tube 30, with the resulting flaps defining the tabs 38. Of course, any suitable structure or fitting may be used that is integral with or attached to the tube 30, and operative to move the tube over the dilator in a proximal direction.

The proximal extremity of the tube 30 is pulled onto the tapered conical surface of the dilator. Since the distal extremity of the tube 30 is smaller in cross section than the adjacent tapered surface of the dilator the tube cannot be pulled any farther in a proximal direction. In the particular embodiment illustrated, the difference in diameters between the complemental portions of the tube 30 and the dilator 22 constitute a constraining means 28 which prevents further movement of the tube over the dilator. However, other means may be employed to accomplish this if desired. It is visualized that other means for such interengagement could be utilized to prevent proximal movement of the tube beyond a certain point on the dilator.

The constraint on the tube offered by the stop section or constraining means 28 is important when the dilator and tube are thrust through body tissue and into the trachea. Without some form of constraining means 28 or its equivalent, the very flexible tube 30 would longitudinally collapse and collect in "accordion" fashion at the proximal end of the dilator.

Figure 5:
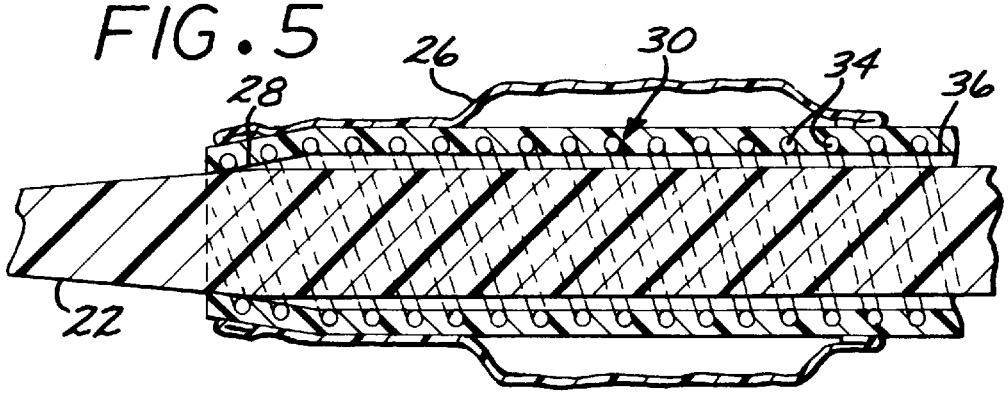
FIG. 5 is an enlarged view taken along the line 5—5 of FIG. 4, and showing the engagement between the distal end of the tube with the dilator stop section, and further showing the inflatable cuff as it would appear when inflated, modified to include a stiffening section.
Figure 5A:
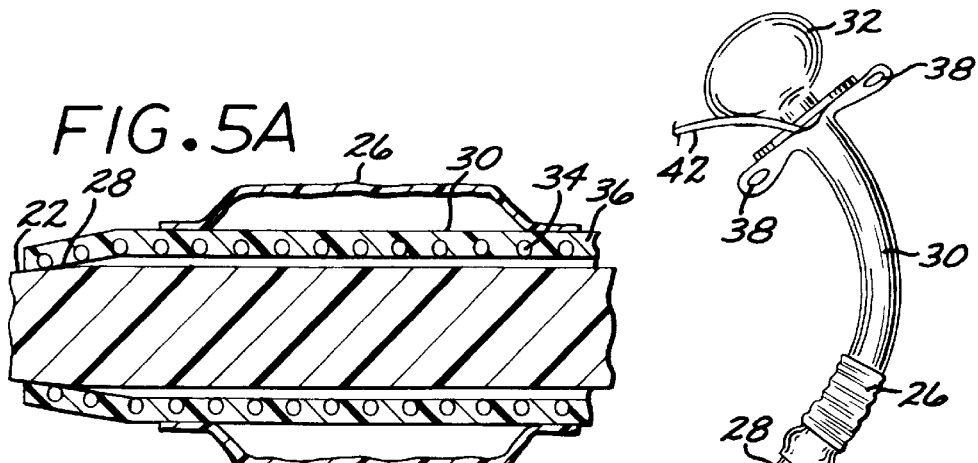
FIG. 5A is a view similar to FIG. 5, but showing the inflatable cuff as it would appear according to the prior art.

As best seen in FIG. 5, and as explained in detail in U.S. Pat. No. 5,537,729, the tube 30 includes a wire coil 34 of stainless steel spring material coated with an impervious or fluid tight polymeric material 36. This combination produces a flexible tube 30 which is ultra thin walled and not easily susceptible to collapsing or kinking. It is so thin walled that its internal diameter is much larger than that of prior art breathing tubes, increasing air flow and reducing airway resistance.

According to U.S. Pat. No. 5,537,729 the wall thickness of the patented tube compared to structures of the prior art is 50–80% less, resulting in a two to four fold decrease in air flow resistance.

With the thin walled tube in position on the dilator, the syringe 20 is removed, and the needle 10 split apart along the score line 14. This enables the leader 24 and trachea tube 30 to be progressively separated from the needle as the needle is withdrawn from the trachea tube.

The dilator 22 and the tube 30 mounted to it can now be thrust inwardly into the trachea and through the body tissue surrounding it. The dilator 22 follows the path defined by the leader 24, enlarging the leader opening in the process.

In a tracheostomy procedure, it is desirable to mount a passage occluding means such as an inflatable annular bladder or cuff 26 affixed to the outer surface of the breathing tube 30. The proximal end of the cuff 26 preferably extends beyond the proximal end of the tube 30. Once in the trachea, the cuff can be inflated by means well known in the art to occlude the annulus or space defined between the wall of the trachea and the breathing tube.

The sleeve of the cuff 26 is cemented or otherwise adhered to the outer surface of the trachea breathing tube 30 and extends to the distal end of the trachea tube at the stop section, adding stiffness to the tube. Although not shown, an opening is formed in the wall of the tube 30 to provide communication between the interior of the cuff and the distal end of an air tube 42. In the embodiment illustrated, the air tube 42 is connected to a suitable air inflating syringe (not shown) for selective inflation.

Figure 12:
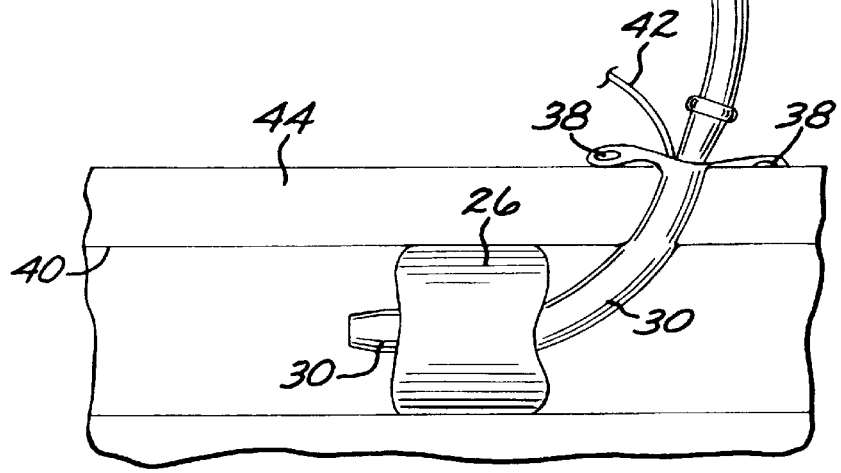
FIG. 12 is a view similar to FIG. 11, but illustrating the dilator partially withdrawn from the tube.

When the cuff 26 is deflated, it is folded in collapsed form on the trachea tube 30 adjacent the distal extremity of the tube 30. It is dimensioned for easy insertion into the trachea along with the dilator and trachea tube. In addition, the cuff 26 serves another purpose. Use of the ultra thin, flexible and longitudinally collapsible tube 30 is made much easier if its distal segment is reinforced, as seen in FIG. 5, as by thickening it in the region of the constraining means 28 and by attachment of the cuff 26 at its opposite extremities to the tube 30. The resulting rigidity helps the tube 30 separate more easily from the dilator 22. This occurs when the dilator 22, the collapsed cuff and the tube 30 are located in the trachea, and the dilator 22 is pulled axially outwardly by pulling upon the knob or handle 32, as seen in FIG. 12. This separate the dilator 22 from the tube 30.

Figure 13:
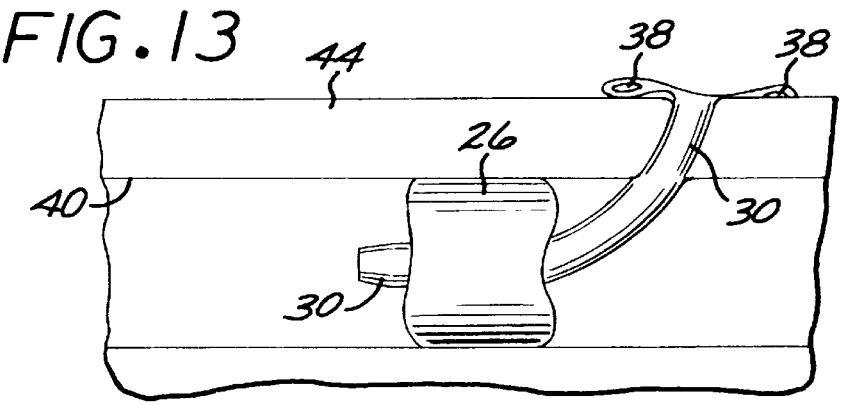
FIG. 13 is a view similar to FIG. 12, but illustrating the dilator removed from the tube to leave the tube in position in the trachea.

As the dilator 22 is withdrawn, the tube 30 might be expected to be withdrawn with it. However, this is prevented by the pressure of the surrounding tissue 44 upon the inserted tube 30, as seen in FIG. 13. The wire reinforcement of the tube prevents it from being collapsed by such pressure. Thus, the dilator is removed and the tube 30 is retained within the trachea so that the patient can breath through it, or a respirator (not shown) can be attached to the tube 30 and operated in known fashion to move air through the patient's airways.

Utilizing the foregoing just described combination of the unique flexible trachea breathing tube 30, the special dilator 22, and the splittable needle 10, a number of important advantages are realized. In particular, the wall thickness of the trachea breathing tube is reduced from approximately 2 mm to 0.2 mm, which greatly reduces the resistance of air flow through the tracheal lumen. In addition, the reduced outer diameter makes it easier to thrust the dilator and trachea tube into the trachea through body tissue.

What is claimed is:

1. A method for performing a tracheostomy comprising the steps of:

placing a radially reinforced, resilient, longitudinally collapsible and ultrathin walled trachea tube upon an elongated dilator having a distal extremity by sleeving the trachea tube over the distal extremity and onto the proximal extremity of the dilator;

thrusting needle means through the wall of the trachea and into the trachea;

inserting the distal extremity of the dilator through the needle means;

separating the needle means from the dilator and withdrawing the needle means from the trachea;

thrusting the dilator and trachea tube through the wall of the trachea and into the trachea;

providing constraining means having portions on the dilator and on the trachea tube engageable to constrain the trachea tube from separation from the distal extremity of the dilator and folding up in accordion fashion on the trachea tube when the dilator and the trachea tube are thrust into the trachea; and withdrawing the dilator from the trachea, leaving the trachea tube in the trachea.

2. A method for performing a tracheostomy according to claim 1, and further including the step of allowing the wall of the trachea to expand against and squeeze upon the trachea tube to prevent the trachea tube from being withdrawn from the trachea along with the dilator.

* * * * *

UNITED STATES PATENT AND TRADEMARK OFFICE
CERTIFICATE OF CORRECTION

PATENT NO. : 6,382,209 B1
DATED : May 7, 2002
INVENTOR(S) : Frederic J. Toye

It is certified that error appears in the above-identified patent and that said Letters Patent is hereby corrected as shown below:

Column 3,
Line 55, after "placement of the dilator and" delete "breathing";
Line 67, after "percutaneous tracheostomy." insert -- The method and apparatus are particularly adapted for use by persons not having extensive surgical training. --;

Column 4,
Lines 5-8, delete second paragraph ;

Column 6,
Lines 3 and 4, delete "thin, flexible and longitudinally collapsible" and insert -- thin and flexible -- ; and
Line 13, delete "separate" and insert -- separates --.

Signed and Sealed this

Twenty-ninth Day of June, 2004

JON W. DUDAS
*Acting Director of the United States Patent and Trademark Office*